United States Patent [19]

Mahany

[11] 4,265,125

[45] May 5, 1981

[54] FLOWMETER METHOD AND APPARATUS

[76] Inventor: Richard J. Mahany, 1341 Harold Dr., SE., Cedar Rapids, Iowa 52403

[21] Appl. No.: 63,007

[22] Filed: Aug. 2, 1979

[51] Int. Cl.³ .......................... G01F 1/32; G01F 9/24; G01F 29/00
[52] U.S. Cl. ............................... 73/861.03; 73/32 A; 73/339 A; 73/861.23
[58] Field of Search ................ 73/24, 30, 32 R, 32 A, 73/194 VS, 194 M, 339 A, 861.03, 661.23

[56] References Cited

U.S. PATENT DOCUMENTS

| | | | |
|---|---|---|---|
| 2,865,196 | 12/1958 | Bordenave et al. | 73/53 |
| 2,991,650 | 7/1961 | Katzenstein | 73/194 |
| 3,984,895 | 10/1976 | Grice, Jr. | 73/32 |

Primary Examiner—Herbert Goldstein
Attorney, Agent, or Firm—Griffin, Branigan & Butler

[57] ABSTRACT

A flowmeter determines the density of a fluid stream by periodically shifting a carrier sonic signal at a carrier modulation frequency and detecting the peak received energy after the carrier sonic signal traverses the stream. The flowmeter may additionally determine the temperature, volumetric flow, and mass flow of the fluid stream.

6 Claims, 5 Drawing Figures

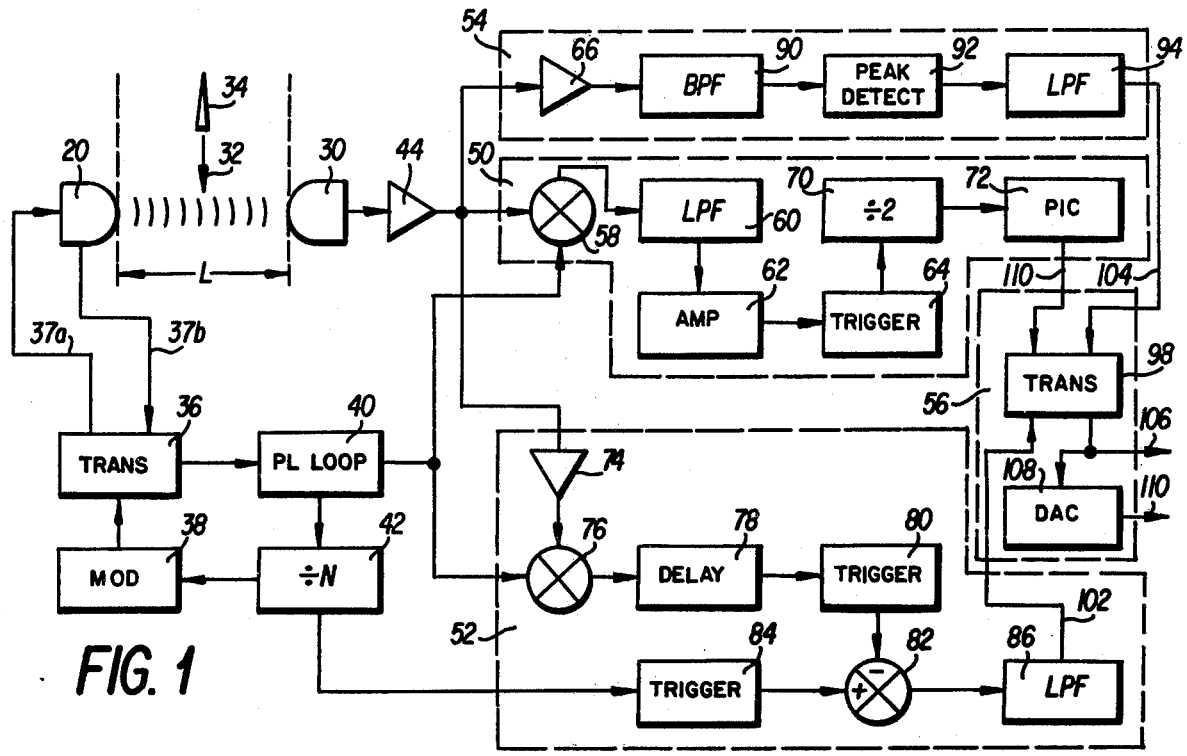
FIG. 1
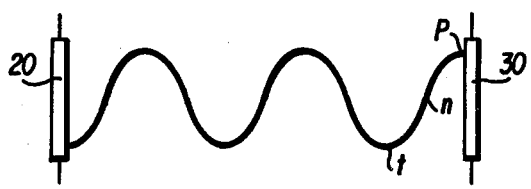
FIG. 2a
FIG. 2b
FIG. 2c
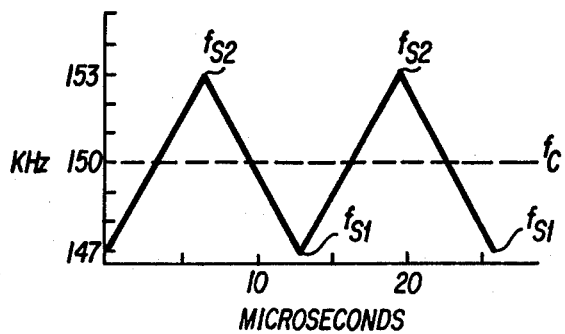
FIG. 3

FLOWMETER METHOD AND APPARATUS

BACKGROUND OF THE INVENTION

This invention pertains to flowmeters, particularly flowmeters wherein a sonic signal is used to determine either the density or pressure of a fluid.

Numerous prior art flowmeters determine the density of a fluid by traversing a sonic signal from a transmitting transducer through a fluid stream to a receiving transducer and using the received energy as a measure of the fluid density. In these flowmeters it is known that a voltage drop across the receiving transducer is a linear function of the acoustical impedance ($\rho c$) of the fluid where $\rho$ is the density of the fluid and c is the speed of sound in the fluid. It is also known that the acoustical impedance $\rho c$ is directly proportional to the pressure P exerted by the fluid and inversely proportional to the square root of the absolute temperature T of the fluid.

In these prior art flowmeters as basically described, the sonic, or acoustic, signal is generally reflected back and forth between the transducers, resulting in the formation of a standing wave pattern. The reflection may be caused by such factors as the dissimilar properties of the air or other medium and the transducers, transducer mounting techniques, and the preferred facing-orientation of the transducers. Although the sonic signal may have been transmitted at a relatively constant frequency, the standing wave superimposed thereon has peaks, nulls and troughs. As a result, the energy received at the receiving transducer depends to a significant degree on whether the receiving transducer is looking at any one moment at a standing wave peak, a trough, or at some point in between.

Various attempts have been made to negate the effect of standing waves in density-determining flowmeters. In some flowmeters pulse transmission may be employed so long as the pulse length is made less than the propagation time for the pulse to travel from the transmitting transducer to the receiving transducer and be reflected back. In a continuous wave transmission mode, such as in the illustrated embodiment of the invention, the standing wave may be partially negated by matching the transducers as closely as possible to the fluid impedance; by slightly tilting the transducers so that any reflected energy will not be returned to the other transducer; by placing absorption materials on the walls of the flowmeter which define the fluid stream and house the transducers; and, by placing a coupling material on the faces of the transducers. However, these techniques have not eliminated the standing wave influence to the degree required in many operating environments.

As noted above, the velocity of sound in a fluid is proportional to the fluid temperature. Hence, when the fluid temperature changes, the standing wave pattern shifts. This standing wave shift is particularly noticeable in some operating environments where the temperature of the fluid may change approximately by a factor of 2. A prime example is the air intake of an automotive internal combustion engine where the temperature ranges from approximately 220° Kelvin to the neighborhood of 400° Kelvin. Over such a broad temperature range the acoustic velocity in the fluid may change by as much as 33%.

Sonic flowmeters typically transmit frequencies approximately 150 KHz., the optimum frequency being based on a number of factors including signal coupling and absorption-attenuation characteristics. At these transmitted frequencies the resultant transmitted acoustic wavelengths are fairly small. Accordingly, the wavelengths of the standing wave pattern are even smaller—about half that of the transmitted wave frequency.

With these small wavelengths and over these temperature ranges, there is a change in the number of standing wave wavelengths—generally a change of 8 to 12 wavelengths—occuring between the transducers. Hence, as the temperature changes and the standing wave shifts, there is no assurance that the receiving transducer will consistently see a standing wave peak. As the standing wave seen by the receiving transducer shifts, the relative energy received varies accordingly. Hence, a density-measuring sonic flowmeter operating at a fixed frequency is subject to considerable inaccuracy due to the temperature dependency of the standing wave.

Therefore, it is an object of this invention to achieve an accurate determination of fluid density in a sonic flowmeter by eliminating the temperature dependent nature of the relative energy measurement.

In flowmeters of this type which also measure the fluid temperature by detecting the transit time of the sonic signal between the two transducers (by comparing the phase of the received signal to the phase of the transmitted signal), an ambiguity occurs in the transit time measurement. This ambiguity results from the significant propagation delay time of the transmitted signal as compared to the short time period for the transmitted acoustic frequency.

Therefore, another object of this invention is the elimination of the ambiguity involved in the fluid temperature measurement when using a flowmeter which detects a phase shift due to a propagation delay time as a sonic signal traverses the fluid.

One of the advantages of the invention is the utilization of a single sensor for the measurement of volumetric flow, fluid density, and/or fluid temperature, such measurements being spacially made in the same region.

Another advantage of the structure of the invention is the realization of substantial cost savings by using a single sensor to perform measurements heretofore performed by a plurality of sensors.

SUMMARY

The sonic flowmeter about to be described modulates the frequency of the transmitted carrier sonic signal in order to shift the carrier signal about a reference average carrier frequency. The structure also incorporates a peak detection circuit which filters components caused by vortices which modulate the sonic signal; detects the relative energy received at the peaks of the filtered received sonic signal; and, creates a D.C. voltage which is averaged over a range of peak voltages for use as an indication either of the fluid density or the fluid pressure.

The carrier sonic signal is shifted about the reference average carrier frequency through a range of frequencies necessary to move the standing wave sufficiently to assure that the receiving transducer will see a standing wave peak. Thus, the temperature-dependent nature of the relative energy measurement is eliminated to provide an accurate indication of either fluid density or pressure.

In order to resolve the ambiguity associated with the transit time measurement (and thus the fluid temperature measurement proportional thereto) a signal is generated indicative of changes in the rate at which the frequency of the sonic signal is received with respect to the reference average carrier frequency. From this signal is subtracted the modulation frequency of the carrier signal as the carrier is shifted through the range of frequencies. The result is the phase difference of the transmitted sonic signal due to the propagation delay time. By giving the range of frequencies a longer period than the propagation delay time of the sonic signal, the ambiguity is eliminated.

BRIEF DESCRIPTION OF THE DRAWINGS

The foregoing and other objects, features, and advantages of the invention will be apparent from the following more particular description of preferred embodiments as illustrated in the accompanying drawings in which like reference characters refer to the same parts throughout the various views. The drawings are not necessarily to scale, emphasis instead being placed upon illustrating the principles of the invention.

FIG. 1 is a block diagram illustrating a flowmeter of the invention;

FIGS. 2a, 2b, and 2c are diagrammatic illustrations of representative standing wave patterns occuring in a flowmeter of the invention; and, FIG. 3 is a diagrammatic illustration representing a range of frequencies through which the carrier frequency is shifted.

DETAILED DESCRIPTION OF THE DRAWINGS

FIG. 1 illustrates a flowmeter which comprises sonic signal transmitting means and sonic signal receiving means, shown as transmitting transducer 20 and receiving transducer 30 respectively, separated from one another by a distance L along an axis substantially perpendicular to the direction of fluid flow as indicated by arrow 32. A vortex strut 34 is located upstream in the fluid so that Karman vortices are formed in the wake of the strut 34. The Karman vortex phenomenon and suitable apparatus for incorporating the transducers 20,30 and the vortex strut 34 are explained and illustrated in U.S. Pat. No. 3,680,375 to Joy et al. which is assigned to the assignee of the present application and incorporated herein by reference.

The transmitting transducer 20 is connected to a transmitter 36 by wires 37a and 37b; and, transmitter 36 is in a circuit loop with a modulation means, such as carrier shift modulator 38, a phase lock loop circuit 40, and a frequency divider 42.

The receiving transducer 30 is connected to an amplifier 44, which is in turn ultimately connected to a volumetric flow measurement circuit 50, a temperature measurement circuit 52, a relative energy measurement circuit 54, and a mass flow computation circuit 56, each of the circuits being described in detail hereinafter.

The volumetric flow measurement circuit 50 comprises a mixer 58 having one input terminal connected to an output terminal of amplifier 44 and a second input terminal connected to the phase lock loop circuit 40. An output terminal of mixer 58 is sequentially connected to a low pass filter 60, an amplifier 62, a Schmidt trigger 64, a frequency divider 70, a pulse insertion circuit 72, and, finally, to the mass flow computation circuit 56.

The temperature measurement circuit 52 comprises a clipping amplifier 74 which is connected intermediate the amplifier 44 and a first input terminal of mixer 76. A second input terminal of mixer 76 is connected to the phase lock loop circuit 40. The output terminal of mixer 76 is sequentially connected to a delay insertion circuit 78, a Schmidt trigger 80, and to a first input terminal of mixer 82. A second input terminal of mixer 82 is connected to Schmidt trigger 84 which in turn is connected to the frequency divider 42. The output terminal of mixer 82 is connected to a low pass filter 86, and then to the mass flow computation circuit 56.

The relative energy measurement circuit 54 comprises a bandpass filter 90 which is connected to amplifier 66, peak detection circuit 92 connected to filter 90, and a low pass filter 94 which is connected intermediate peak detection circuit 92 and the mass flow calculation circuit 56.

The mass flow computation circuit 56 comprises a data transmitter 98 which includes a pulse width modulator, an amplitude modulator, a one-shot, and an analog switch (not shown). Data transmitter 98 is connected to the volumetric flow measurement circuit 50 by line 100, to the temperature measurement circuit 52 by line 102, and to the relative energy measurement circuit 54 by line 104. Digital output from the data transmitter 98 may be taken at line 106 or applied to an analog converter 108 for the production of an analog signal on line 110.

In operation, the transmitter 36 generates a carrier frequency approximating the resonant frequency of the transmitting transducer and applies the same to transducer 20 on line 37a. The transmitter 36 monitors the resonant frequency of the transmitting transducer 20 on line 37b, and adjusts the transmitter signal to take into consideration any changes in the resonant frequency due to aging of the transducer. As will be explained very shortly, this operating carrier frequency is not constant but rather constantly shifts through a specified range of frequencies.

When the electrical signal corresponding to the actual carrier frequency is generated by transmitter 36 and applied to the transmitting transducer 20, the trasducer 20 generates a sonic signal which traverses the fluid stream and is received at the receiving transducer 30. In this respect, as noted in U.S. Pat. No. 3,680,375 to Joy et al, the term "sonic" means acoustic, ultra-sonic and sub-sonic waves, with ultra-sonic waves being preferred.

While much of the sonic signal is detected at the receiving transducer 30, at least some portion of the signal is reflected back in the direction of the transmitting transducer 20 by reason of the considerations discussed above. The continued reflection of the continually transmitted sonic signal results in the establishment of a standing wave pattern in the fluid stream between the transmitting transducer 20 and the receiving transducer 30.

FIGS. 2a shows an exemplary standing wave pattern established between the transmitting transducer 20 and the receiving transducer 30. For purposes of illustration the standing wave pattern of FIG. 2 is shown to have three peaks, one peak p of which occurs at the receiving transducer 30, three troughs t, and a null n occuring between each peak and trough. However, as the temperature of the fluid stream changes, the speed of sound in the fluid changes, causing the standing wave pattern to shift as in FIG. 2b. Now the receiving transducer 30 no longer sees peak p of the standing wave, but another portion of the standing wave indicative of another energy level. Thus, as the standing waves continue to shift in similar manner as the temperature continues to change, the receiving transducer 30 is unpredictably subjected to standing wave amplitudes ranging from a peak to a null. As a result, the relative energy measurement, and hence the fluid density or pressure measurement, can be erroneously influenced by the standing wave pattern.

In order to eliminate the effect of the standing waves, the carrier shift modulator 38 (FIG. 1) shifts the frequencies generated by transmitter 36 through a range of frequencies. In a preferred embodiment a typical reference average operating frequency $f_C$ approximates 150 KHz. and can be precisely determined by a phase lock loop circuit 40 which receives the signal generated by transmitter 36. The degree of requisite frequency shift is established by the frequency divider 42 which divides the reference average carrier frequency signal $f_C$ received from circuit 40 by a pre-calculated integer constant N to yield a modulation frequency $f_M$. In a preferred embodiment, $f_M$ approximates 7.5 KHz. Thus, the actual carrier frequency $f_T$ is in a range $$f_{S1} \leq f_T f_{S2}$$

where $f_{S1}$ and $f_{S2}$ are chosen to create more than a quarter-wavelength standing wave change at the receiving transducer 30. In a preferred embodiment a typical value of N approximates 20; $f_{S1}$ approximates 147 kHz; and, $f_{S2}$ approximates 153 KHz. Of course, the choice of $f_{S1}$ and $f_{S2}$ is limited by the passband of the transducers, and for best results should be well within the appropriate band width of the transmitting transducer 20, usually about 3dB.

FIG. 3 shows a sample segment of the actual carrier frequency as it ramps through the lowest frequency $f_{S1}$ to a peak $f_{S2}$, and back to complete a first cycle at $f_{S1}$, and then sweeps an additional or second cycle. In the illustrated embodiment each cycle shown in FIG. 3 approximates 130 microseconds, which is sufficiently greater than the 80 to 100 microseconds typically required for the sonic signal to traverse the distance L between the transmitting transducer 20 and the receiving transducer 30 (of course, when the distance L is changed, the cycle may also require adjustment).

As the actual carrier frequency $f_T$ ramps or shifts through the range from $f_{S1}$ to $f_{S2}$, the standing wave pattern begins to change. Specifically, the standing wave peak to peak wavelength difference changes as $f_T$ shifts. Assume for illustration that the standing wave pattern previously appeared as in FIG. 2b. Then, due to a temperature change, for some $f_T$ between $f_{S1}$ and $f_{S2}$ the standing wave shifts due to the change in $f_T$ and has a peak p' occuring at the receiving transducer 30 (see FIG. 2c). Thus, the receiving transducer 30 sees a peak between each frequency ramp from $f_{S1}$ up to $f_{S2}$ and between each frequency ramp from $f_{S2}$ down to $f_{S1}$ despite any standing wave shifts caused by temperature fluctuations.

As the transmitting transducer 20 directs a sonic signal through the fluid stream and toward the receiving transducer 30, several phenomena occur in addition to the creation of the standing waves. First, the transmitted signal $f_T$ is modulated at a modulation frequency $f_A$ by the Karman vortices generated by the strut 34 in the manner described in U.S. Pat. No. 3,680,375 to Joy et al. The Karman vortex modulation frequency $f_A$ is additional to and distinct from the modulation frequency $f_M$ generated by shift modulator 38.

Secondly, the phase of the transmitted signal $f_T$ undergoes a shift or phase difference $\phi_T$ as the transmitted signal $f_T$ traverses the distance L through the fluid stream from the transmitting transducer 20 to the receiving transducer 30. Thus, the receiving transducer 30 receives a composite signal $f_T + f_A + \phi_T + f_N$, where $F_N$ represents various noise components to be discussed hereinafter. This signal is applied first to amplifier 44 for suitable amplification and then in parallel to the volumetric flow measurement circuit 50, the temperature measurement circuit 52, and the relative energy measurement circuit 54.

The volumetric flow measurement circuit 50 functions to detect the modulation frequency $f_A$ which is a measure of the rate of the generation of Karman vortices in the fluid stream. In a preferred embodiment $f_A$ may be in a neighborhood, for example, of 4.5 KHz. Using the modulation frequency $f_A$ the circuit 50 creates a digital pulse output train at a rate which is proportional to the volumetric flow V of the fluid.

In circuit 50 the composite signal received from amplifier 44 is applied to a first input terminal of the mixer 58. Mixer 58 also receives, at a second input terminal, the reference average carrier frequency $f_C$ which is derived from the phase lock loop circuit 40. Using classical mixing techniques, the mixer 58 generates an output signal equal to the rate at which the frequency $f_T + f_A$ changes with respect to the frequency $f_C$. Mixer 58 keys on the rate of change of the respective frequencies instead of the absolute values thereof. Hence, mixer 58 generates a signal $f_M + f_A$.

The output signal from mixer 58 is filtered by a low pass filter 60 which eliminates the modulation frequency component $f_M$ and the noise component $f_N$, thereby leaving the frequency component $f_A$ which is due to the Karman vortex modulation frequency alone. The filtered signal is then sent to amplifier 62 for suitable amplification and then to Schmidt trigger 64 which provides a square wave representation of $f_A$.

In route from the Schmidt trigger 64 to the mass flow computation circuit 56 the square wave representation $f_A$ passes through a pulse insertion circuit 72 which provides greater resolution for the mass flow parameter V. However, because the pulse insertion circuit 72 requires a symmetrical output frequency, a frequency divider 70 is interposed between the Schmidt trigger 64 and the pulse insertion circuit 72. Accordingly, the frequency divider 70 divides $f_A$ by 2. The pulse insertion circuit 72 (which is actually a frequency lock loop) then locks on an average frequency which is actually eight times the Karman vortex modulation frequency ($8f_A$). As a result, the mass flow computation circuit 56 can now average over a shorter time period, i.e. the output will track more quickly. Advantageously, the volumetric flow measurement circuit 50 is now able to provide an output not having missing pulses. This output signal is applied to the mass flow computation circuit 56 along line 100 which carries a train of pulses at a rate proportional to the volumetric flow V.

The relative energy measurement circuit 54 functions to detect the relative energy received which is a measure of the density, or pressure, of the fluid. Using the received transmitted frequency $f_T$, the circuit 54 creates a D.C. voltage output proportional to the density, or pressure, of the fluid.

The relative energy measurement circuit 54 receives from amplifier 66 the composite received signal which includes the transmitted sonic signal $f_T$, the Karman vortex modulation frequency $f_A$, and various noise components collectively referred to as $f_N$. Actually, the noise components stem from electrical and mechanical factors which degrade the quality of the signal. These components, although fairly small (less than 10% of the total received signal), should be eliminated since it is preferred that the relative energy measurement circuit 54 have a resolution accuracy on the order of 1 to 2%.

The noise components $f_N$ actually stem from two effects. The first noise component effect is a low frequency audio component which is added, or summed, to the carrier signal. The second noise component effect arises from the modulation of the carrier signal. The first noise component effect is eliminated by the bandpass filter 90, but the second noise component effect is passed on to the peak detector 92 and eventually averaged out by the low pass filter 94.

The purpose of the peak detection circuit 92 is to filter out the energy amplitude associated with the Karman vortex modulation frequency $f_A$ and to determine the relative peak energy of the filtered received signal. A DC output voltage from peak detection circuit 92 is then applied to the low pass filter 94 which averages the DC signal and provides a long term time average of the peak DC value. By so averaging the DC signal, the low pass filter 94 eliminates the second noise component effect due to the modulation of the carrier signal. The output of the low pass filter 94 is a DC voltage signal proportional to the relative energy received, and thus the fluid density; and is applied on line 104 to the mass flow computation circuit 56.

The temperature measurement circuit 52 functions to detect the phase shift of the transmitted signal due to the propagation delay time (transit time) of the sonic signal as it traverses the distance L between the transducers. Using the phase shift $\phi$, the circuit 52 creates a D.C voltage level proportional to this transit time (which is also inversely proportional to the square root of the absolute temperature of the fluid).

The temperature measurement circuit 52 receives the composite received signal from amplifier 44 at clipping amplifier 74. Clipping amplifier 54 effectively eliminates all the Karman vortex modulation frequency component ($f_A$) and leaves only the transmitted signal $f_T$ which has been phase modulated. This signal ($f_T + \phi_T$) is applied as a first input to mixer 76 which also receives as a second input the reference average carrier frequency $f_C$ as derived from the phase lock loop circuit 40. By classical mixing techniques the mixer generates a signal indicative of the rate at which $f_T + \phi_T$ changes with respect to the reference average carrier frequency $f_C$. Thus, the absolute values of $f_T$, $f_C$, $\phi_T$ are not significant, only the variation in their rates.

The resultant signal is $f_M + \phi_T$, since the rate at which $f_T$ changes with respect to $f_C$ is $f_M$. This signal is applied to a delay insertion circuit 78 which provides calibration of the temperature measurement circuit 52 by taking into consideration the signal delay which occurs upon initial activation of the flowmeter as the first transmitted signal traverses the distance L between the transmitting transducer and the receiving transducer 30.

From circuit 78 the output is first fed to Schmidt trigger 80, which creates a square wave for the signal $f_M + \phi_T$, and then fed as the first input to the mixer 82. The second input of the mixer 82 is a square wave representation of the signal $f_M$ created by the Schmidt trigger 84 which received the $f_M$ value from the frequency divider 42. Mixer 82 functions as a logic gate to generate a signal $\phi_T$ which is applied to the low pass filter 86 to eliminate noise components and establish (on line 102) a signal having a D.C. voltage proportional to the transit time of the sonic signal (and thus inversely proportional to the square root of the temperature of the fluid stream).

As described above, each of the circuits 50, 52, and 54 transmits a respective signal to the mass flow computation circuit 56. Specifically, the volumetric flow measurement circuit 50 transmits a signal on line 100 comprising a train of pulses at a rate which is proportional to the volumetric flow of the fluid. The temperature measurement circuit 52 transmits on line 102 a D.C. voltage proportional to the transit time of the signal as it traverses the fluid stream, (this voltage level also being inversely proportional to the square root of the temperature of the fluid).

The relative energy measurement circuit 54 transmits on line 104 a DC voltage signal having a magnitude proportional to the relative received energy (the acoustical impedance $\rho C$ of the fluid) which is also directly proportional to the pressure P of the fluid and inversely proportional to the square root of the temperature of the fluid.

Thusly described, lines 100, 102, and 104 feed the data transmitter 98 which creates a signal proportional to the mass flow M of the fluid according to the mathematical relationship $$V \cdot \frac{1}{\sqrt{T}} \cdot \frac{P}{\sqrt{T}} = V\frac{P}{T} = M$$

In this respect, the digital pulse signal for the mass flow M may be taken along line 106 or applied to a converter 108 which integrates the signal and produces an analog output having a DC value proportional to the mass flow M on line 110.

The data transmitter 98 actually comprises a pulse width modulator, an amplitude modulator, a one-shot, and an analog switch (none of which are shown). The one-shot has a variable pulse width controlled by the input on line 102 and is clocked by the input on line 100. The output of this one-shot device goes to an analog switch which generates a pulse height proportional to the fluid density as received on line 104.

From the foregoing it should be understood that the invention is not limited to mass flowmeters per se, but pertains primarily to the accurate measurement of the fluid density; fluid pressure; and, fluid temperature.

Moreover, it should be noticed that various mathematical constants, such as those employed in the mathematical relationships derived and explained in U.S. Patent Application Ser. No. 002,644, filed by Joy et al on Jan. 11, 1979, now abandoned which is assigned to the present assignee and incorporated herein by reference, may be introduced into the circuitry as scaling or gain constants. For example, in the formula for transit time $$t = \frac{L}{\sqrt{KRT_K}}$$

the terms L (the spacing between the transducers), K (the ratio of specific heat), and R (the universal gas constant) may be input as scaling factors in the temperature delay circuit 78. Further, the cross-sectional area of the fluid stream may be represented as a gain constant and applied to the signal emanating from transmitter 98. Likewise, the constants $\mu$ and W in the density formula $$\rho C = \frac{e_0}{\mu W}$$

may be considered as adjustment constants in the peak detection circuit 92.

While the invention has been particularly shown and described with reference to preferred embodiments thereof, it will be understood by those skilled in the art that various alterations in form and detail may be made therein without departing from the spirit of the invention. For example, a filter may be connected between amplifier 44 and mixer 58 to eliminate the phase shift component should such resolution be required in a particular application.

What is claimed is:

1. A method of measuring fluid parameters comprising the steps of:
    directing a carrier sonic signal from a sonic signal transmitting means through a fluid stream;
    receiving said sonic signal at a sonic signal receiving means;
    periodically shifting said carrier sonic signal with respect to a reference average carrier frequency at a carrier modulation frequency so that, during said shift, a standing wave created by said sonic signal has an energy peak at said sonic signal receiving means;
    detecting peak energy received at said sonic signal receiving means;
    using said energy received as a measure of the density of said fluid;
    comparing the rate at which the frequency of the received sonic signal changes with respect to said reference average carrier frequency;
    generating a signal indicative of said rate of change;
    subtracting from said signal indicative of said rate of change the carrier modulation frequency; and,
    using the result of said subtraction as an indication of the absolute temperature of said fluid.

2. The method of claim 1 further comprising the steps of:
    locating a vortex strut in the fluid stream so that Karman vortices are formed in the wake of the strut;
    modulating said transmitted sonic signal by said vortices;
    detecting the modulation frequency of the received sonic signal;
    using the modulation frequency of the received sonic signal caused by said vortices as an indication of the volumetric flow of said fluid;
    filtering from said peak frequency detection a frequency component caused by said vortices which modulate said sonic signal;
    multiplying the volumetric flow of the fluid stream by the fluid density and by the cross-sectional area of the fluid stream and dividing the product by the absolute fluid temperature; and,
    using the result as a measure of mass flow of the fluid stream.

3. A method of measuring fluid parameters comprising the steps of:
    directing a carrier sonic signal from a sonic signal transmitting means through a fluid stream;
    receiving said sonic signal at a sonic signal receiving means;
    periodically shifting said carrier sonic signal with respect to a reference average carrier frequency at a carrier modulation frequency so that, during said shift, a standing wave created by said sonic signal has an energy peak at said sonic signal receiving means;
    detecting peak energy received at said sonic signal receiving means;
    using said energy received as a measure of the density of said fluid;
    locating a vortex strut in the fluid stream so that Karman vortices are formed in the wake of the strut;
    modulating said transmitted sonic signal by said vortices; and,
    filtering from said peak energy a component caused by said vortices which modulate said sonic signal.

4. A fluid flowmeter comprising:
    sonic signal transmitting means for directing a carrier sonic signal through a fluid stream;
    logic signal receiving means for receiving said sonic signal;
    carrier modulation means connected to said sonic signal transmitting means for periodically frequency-shifting said carrier signal with respect to a reference average carrier frequency at a carrier modulation frequency so that a standing wave created by said sonic signal has an energy peak at said sonic signal receiving means;
    means connected to said sonic signal receiving means for detecting an energy peak received at said receiving means, said energy peak representing the density of said fluid
    means to compare the rate at which the frequency of the received sonic signal changes with respect to said reference average carrier frequency, said comparison means generating a signal indicative of said comprison; and,
    means for subtracting from said signal indicative of comparison the carrier modulation frequency to obtain a signal indicative of the absolute temperature of the fluid.

5. The flowmeter of claim 4 further comprising:
    a vortex strut mounted so that Karman vortices are created in the wake of the strut when there is relative movement between the strut and the fluid in which the strut is immersed, said vortices modulating said sonic signal;
    means for detecting the modulation frequency of the received sonic signal and using said modulation frequency as an indication of the volumetric flow of said fluid;
    means for filtering from said peak energy a component caused by said vortices which modulates said sonic signal; and,
    means for multiplying the volumetric flow of the fluid stream by the fluid density and by the cross-sectional area of the fluid stream and dividing the product by the absolute fluid temperature to obtain a quotient which is a measure of the mass flow of the fluid stream.

6. A fluid flowmeter comprising:

sonic signal transmitting means for directing a carrier sonic signal through a fluid stream;

sonic signal receiving means for receiving said sonic signal;

carrier modulation means connected to said sonic signal transmitting means for periodically frequency-shifting said carrier signal with respect to a reference average carrier frequency at a carrier modulation frequency so that a standing wave created by said sonic signal has an energy peak at said sonic signal receiving means;

means connected to said sonic signal receiving means for detecting an energy peak received at said receiving means, said energy peak representing the density of said fluid a vortex strut mounted so that Karman vortices are created in the wake of the strut when there is relative movement between the strut and fluid in which the strut is immersed, said vortices modulating said transmitted sonic signal; and, means for filtering from said peak energy a component caused by said vortices which modulate said sonic signal.

* * * * *